United States Patent [19]

Sekido et al.

[11] Patent Number: 5,015,616
[45] Date of Patent: May 14, 1991

[54] COMPOSITION FOR CATALYTICALLY CLEANING EXHAUST GAS AND TO IMPROVE THE SENSITIVITY OF SENSORS

[75] Inventors: Satoshi Sekido, Yawata; Hirokazu Tachibana, Kyoto; Yasuharu Yamamura, Katano; all of Japan

[73] Assignee: Research Association of Electric Conductive Inorganic Compounds, Tokyo, Japan

[21] Appl. No.: 428,029

[22] Filed: Oct. 27, 1989

Related U.S. Application Data

[60] Continuation of Ser. No. 300,229, Jan. 23, 1989, abandoned, which is a continuation of Ser. No. 74,711, Jul. 17, 1987, abandoned, which is a division of Ser. No. 826,495, filed as PCT JP85/00163 on Apr. 3, 1985, Pat. No. 4,692,429.

[30] Foreign Application Priority Data

Apr. 25, 1984 [JP] Japan ................... 59-84353
May 30, 1984 [JP] Japan ................... 59-109812
Jul. 6, 1984 [JP] Japan ................... 59-140878

[51] Int. Cl.$^5$ ............... B01J 21/06; B01J 23/02; B01J 23/10; B01J 23/78; B01J 23/84; B01J 23/86
[52] U.S. Cl. .................. 502/303; 502/525; 338/34; 422/94; 422/98
[58] Field of Search ............... 502/303, 525; 338/34; 422/94, 98

[56] References Cited

U.S. PATENT DOCUMENTS

4,044,601 8/1977 Sakurai et al. ................ 338/34 X
4,357,426 11/1982 Murata et al. ................. 501/135

FOREIGN PATENT DOCUMENTS

0089199 9/1983 European Pat. Off. .

OTHER PUBLICATIONS

Analytical Chemistry Symposia Series, vol. 17, 1983, pp. 187–192, Elsevier, Amsterdam, NL; Y. Yamamura et al.: "An Element Sensitive to Stoichiometric Composition of Exhaust Gases".
Chemical Abstracts, vol. 95, No. 10, Sep. 7, 1981, p. 147, abstract No. 83548v, Columbus, Ohio, U.S.; & JP-A-81 54 340 (Matsushita Electric Industrial Co. Ltd) 5-14 1981.
Chemical Abstracts, vol. 95, No. 24, Dec. 14, 1981, p. 319, abstract No. 208865e, Columbus, Ohio, U.S.; & JP-A-81 89 048 (Matsushita Electric Industrial Co. Ltd) 07-20-1981.
Yamamura et al., "An Element Sensitive to Stoichiometric Composition of Exhaust Gases", Analytical Chemistry Symposia Series, vol. 17 (1983), pp. 187–192.
Chemical Abstracts, vol. 95, No. 10 (9/7/81), p. 147, Abstract No. 83548v.
Chemical Abstracts, vol. 95, No. 24 (12/14/81), p. 319, Abstract No. 208865e.

*Primary Examiner*—W. J. Shine
*Attorney, Agent, or Firm*—Stevens, Davis, Miller & Mosher

[57] ABSTRACT

This invention provides a composition comprising a mixture or a fired product of a material of the general formula $Sr_{(1+x)/2}La_{(1-x)/2}Co_{1-x}Me_xO_{3-\delta}$ (wherein Me: at least one of Fe, Mn, Cr and V; $0 \leq x \leq 1$; $\delta$: loss of oxygen) and $SrMeO_3$ (wherein Me: at least one of Ti, Zr and Hf), and a catalyst and a multi-functional sensor using such composition. With this composition it is possible to improve the catalytic performance for cleaning exhaust gas from combusters or internal combustion engines and to improve sensitivity or response characteristics of the sensors for dectecting stoichiometric composition.

12 Claims, 18 Drawing Sheets

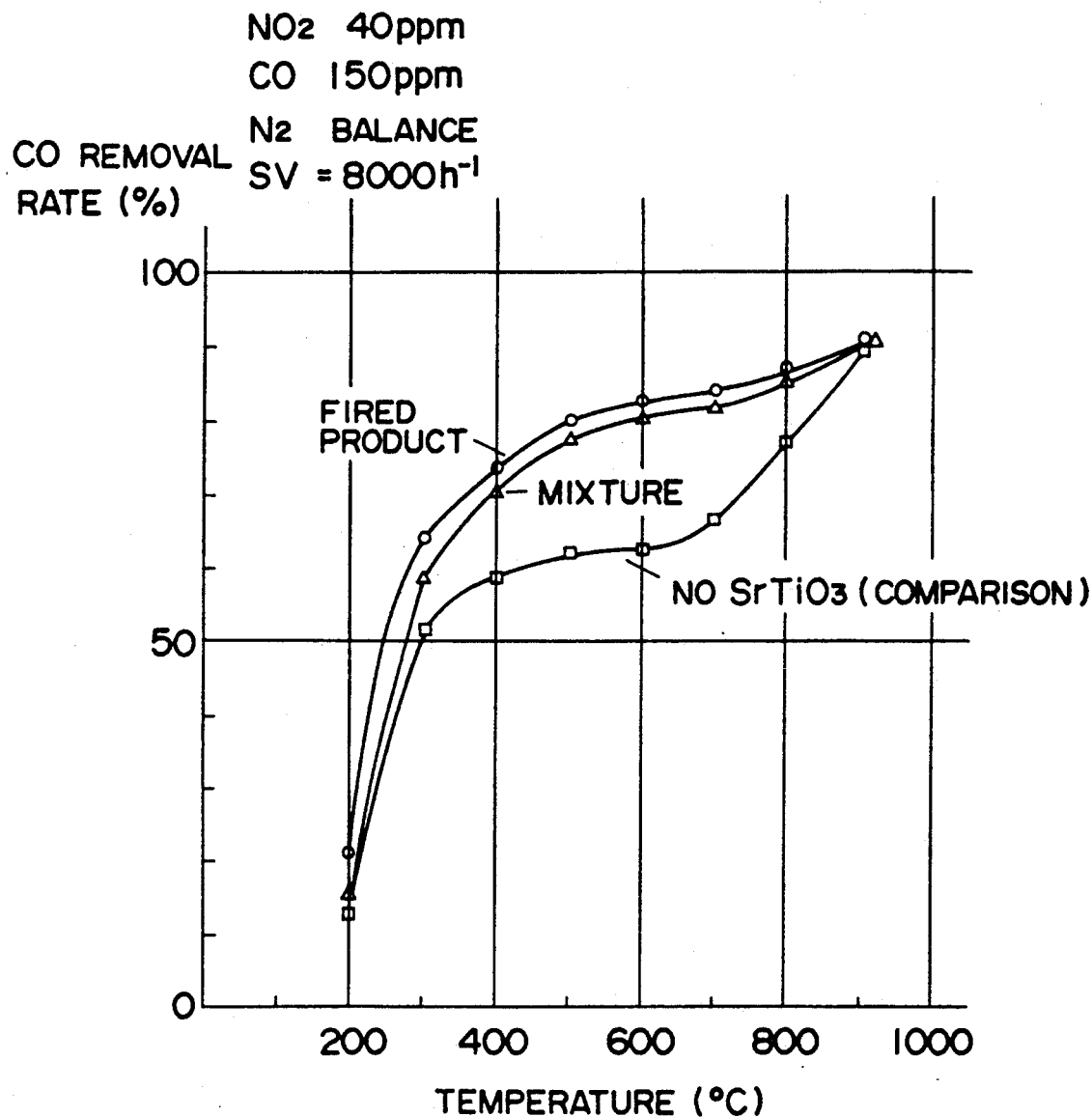

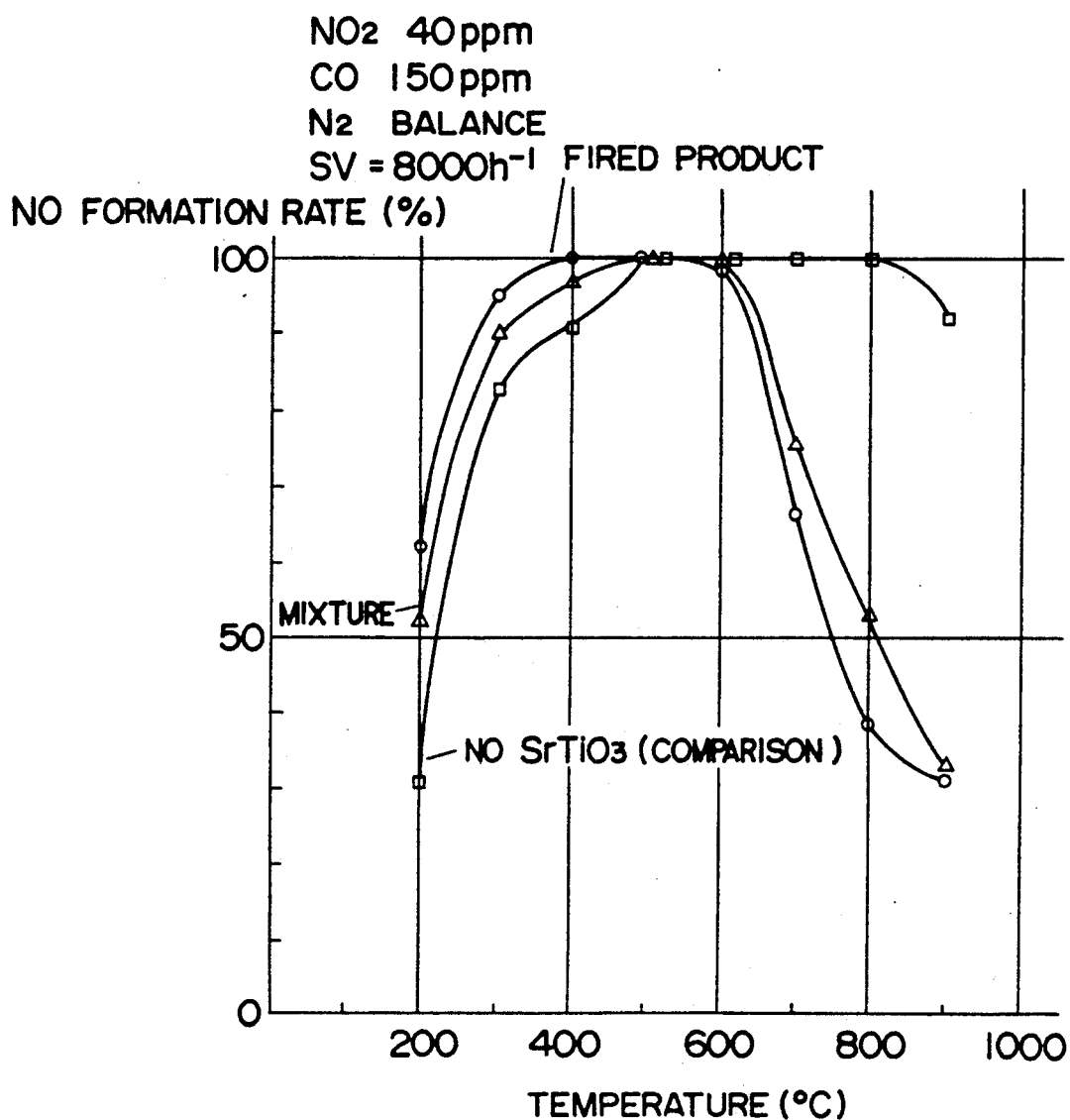

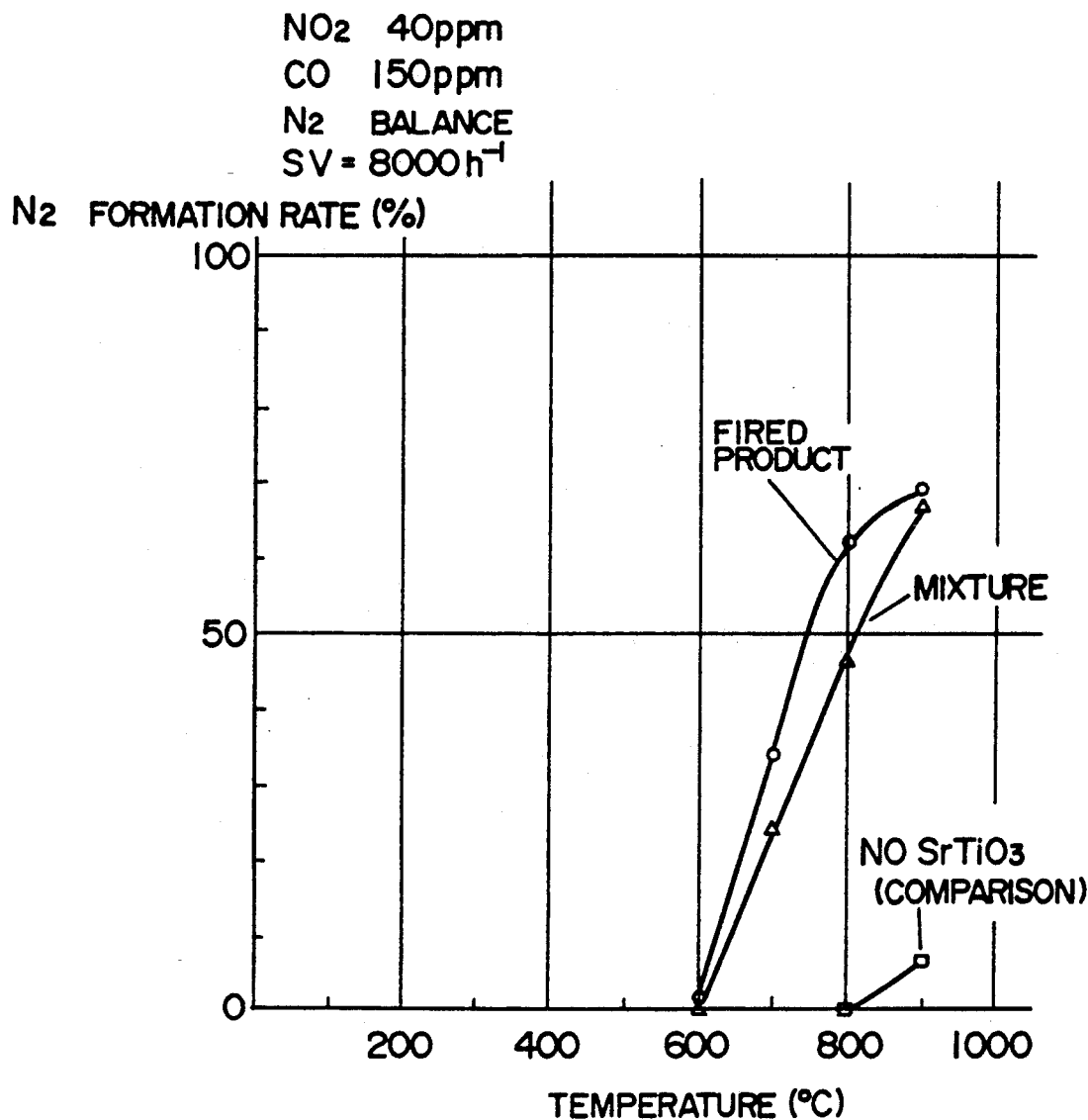

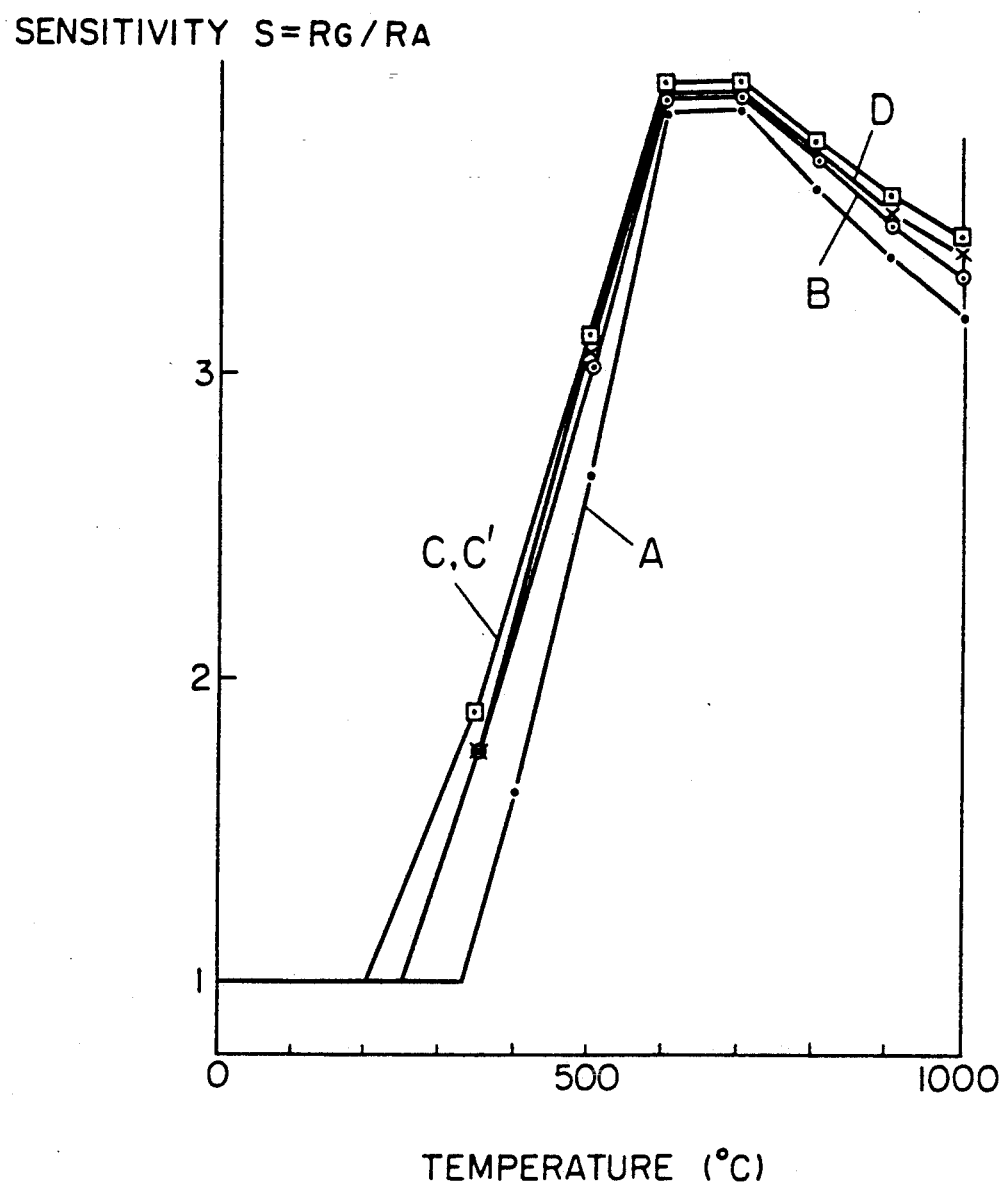

COMPOSITION FOR CATALYTICALLY CLEANING EXHAUST GAS AND TO IMPROVE THE SENSITIVITY OF SENSORS

This application is a continuation of Ser. No. 300,229 filed Jan. 23, 1989, abandoned, which is a continuation of Ser. No. 074,711, filed July, 17, 1987, now abandoned, which in turn is a divisional application of Ser. No. 826,495, filed as PCT JP85/00163 on Apr. 3, 1965, now U.S. Pat. No. 4,692,429.

FIELD OF ART

This invention relates to a composition applicable as a catalyst used by being exposed to combustion exhaust gas for rendering noxious gaseous components therein harmless by a redox (reduction-oxidation) reaction and also applicable as sensors for detecting the stoichiometric air/fuel ratio by measuring a large change in electric resistance.

BACKGROUND ART

Noxious substances such as CO, HC (hydrocarbons) and $NO_x$ are contained in exhaust gas, and catalysts have been used for cleaning such exhaust gas by changing said noxious substances into harmless materials such as $CO_2$, $H_2O$ and $N_2$ through a redox reaction. The catalysts used for this purpose included two types: (1) those using noble metals such as Pt or Pd group metals and (2) those using oxides of transition metals such as Mn, Cu, Ce, etc. Noble metal catalysts are called three-way conversion catalyst and capable of simultaneously eliminating both reductive noxious gases such as CO and HC and oxidative noxious gas such as $NO_x$. It is known, however, that these noble metal catalysts sinter and become aggregated, and lose their catalytic activity when they are exposed to a high temperature. On the other hand, oxide catalysts are used only for eliminating reductive noxious gases.

As to the sensors for detecting the stoichiometic ratio of combustion, there have been known the type in which platinum electrodes are set on both sides of the partition wall of stabilized zirconia solid electrolyte, one of said electrodes being exposed to an atmosphere where the partial pressure of oxygen is constant, such as air, while the other electrode being exposed to exhaust gas, thus forming an oxygen concentration cell, and a sudden change of its electromotive force is utilized for detecting the stoichiometric ratio, and the type in which a sudden change in electric resistance of a metal oxide such as $SnO_2$, $TiO_2$, $MgCr_2O_4$, etc., is utilized. At an air/fuel ratio close to the stoichiometric ratio, the fuel is not perfectly burned and both reductive gases such as CO and HC and oxidative gases such as $O_2$ and $NO_x$ coexist in the exhaust gas, so that there occurs no sudden change of electromotive force or electric resistance from the area of stoichiometric ratio of combustion unless said both types of gases are reacted with each other through the medium of a catalyst. In the systems utilizing the electromotive force of concentration cell, Pt of the electrode on the outside, which contacts with exhaust gas, performs said catalytic action, but in the systems utilizing the electric resistance of the metal oxide, almost no such catalytic action is occurred, so that it was necessary to add a noble metal to the metal oxide.

Recently, attempts have been made to use perovskite type metal oxides for exhaust gas cleaning catalysts or gas sensors, and the present inventors have also filed a patent application featuring the use of a material $Sr_{(1+x)/2}La_{(1-x)/2}Co_{1-x}Me_xO_3$ (Me: Fe, Mn, Cr or V $\delta$: loss of oxygen) (U.S. Pat. Nos. 4,314,996 and 4,485,191). This material exhibits a mixed conductivity of electrons and $O^{2-}$ ions, and the invention of this patent application clarified the relation of such mixed conductivity to the catalytic performance or sensor characteristics and provided a composition with an optimal ratio of components for obtaining the desired characteristics. It is known that generally the oxygen content in a metal oxide varies according to the partial pressure of oxygen in the gas atmosphere, resulting in a change of electric resistance of the metal oxide, and this principle is already applied in various gas sensors. Said material, however, has a quite characteristic property that it can stably maintain the same crystal structure regardless of any voluminous release or takeup of oxygen. In this material, $O^{2-}$ ionic migration (electric conduction) occurs through the deletion of oxygen ions in the crystal lattice, and under high temperature like in exhaust gas, such migration is faster than in other oxides. Therefore, this material shows a high catalytic cleaning performance under high temperature above 500° C., and since the velocity of equilibrium reaction between reductive and oxidative gases is affected by such catalytic performance, it is possible to accelerate the responsiveness of the sensor for detecting stoichiometric composition with no need of using a noble metal catalyst. On the other hand, electric conduction of electrons occurs through conductive pairs of

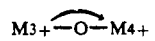

constituted by transition metal M (Co, Fe, Mn, Cr or V) in the B site of said compound oxide $ABO_3$ and oxygen. When the temperature rises or the partial pressure of oxygen in the atmosphere lowers to cause release of oxygen, said conductive pairs disappear to increase electric resistance. To make the average valence number rate of transition metal 3.5 is to mamimize the number of said conductive pairs. The complex oxides of this type allow a greater reversible enlargement of oxygen loss than allowable for other oxides, although only to a point where $\delta$ is 0.5, but if the number of said conductive pairs is maximized, it becomes possible to so much widen the scope of change of resistance by release of oxygen, and this leads to a corresponding increase of sensitivity in use of said material for a sensor. To define the complex oxide composition to $Sr_{(1+x)/2}La_{(1-x)/2}Co_{1-x}Me_xO_{3-\delta}$ was to maximize the deletion of oxygen ions and the number of electron conductive pairs. To substitute Co with one of Fe, Mn, Cr and V was to prevent $\delta$ from becoming greater than 0.5 even in a state of excess reductive gas. The complex oxides of such composition exhibit an excellent catalytic performance and sensor characteristics at high temperatures above 500° C., but the ratio of ion conductivity to electron conductivity is still low level ($10^{-4}$), and it has been required to further increase the ionic transference number for these uses. Also, the high thermal expansion coefficient, $20 \times 10^{-6}$/deg, of said material was a negative factor for combined use with other materials.

The prior art disclosures closest to the present invention are Lucas (U.S. Pat. No. 4,454,494) and Hitachi, Ltd. (U.S. Pat. No. 3,951,603), but these patents are different from the present invention in the following points: in Lucas patent, La is not the essential component, and also the second substance SrMéO$_3$ (Mé: Ti, Zr, Hf) is absent, while Hitachi patent has no SrMéO$_3$.

DISCLOSURE OF THE INVENTION

The present invention provides a composition characterized by the addition of SrMéO$_3$ (Mé: at least one of Ti, Zr and Hf) to the material of the formula Sr$_{(1+x)/2}$La$_{(1-x)/2}$Co$_{1-x}$Me$_x$O$_{3-\delta}$ (Me: at least one of Fe, Mn, Cr and V $\delta$: Loss of oxygen; $0 \leq x \leq 1$ preferably $0 \leq x \leq 0.3$), for further increasing the oxygen ion conductivity and further improving the catalytic performance and sensor characteristics. The addition of SrMéO$_3$, preferably 60–70% my mole, also enables lowering of the thermal expansion coefficient to such an extent that the combination with other materials is made easy. Further, by mixing said both materials in a proper ratio, the resistance in the air is made constant in the high temperature range (400°–1,000° C.) where the stoichiometric composition is detected, thereby the temperature compensation usually required in sensors using TiO$_2$ or SnO$_2$ may be eliminated. The CTR thermistor can operate in the low temperature region to provide the sensor system with the manifold functions such as detection of combustion and cessation of combustion.

The present invention provides a sensor for detecting the air/fuel ratio different from the stoichiometric composition of combustion by combining a sensor using said manifold functioning composition and an oxygen pump.

BRIEF DESCRIPTION OF THE DRAWINGS

FIG. 1 shows the CO removal rate, FIG. 2 shows the NO formation rate, and FIG. 3 shows the N$_2$ formation rate.

FIGS. 4–6 show the catalytic gas cleaning effect by the addition of SrTiO$_3$, determined in the same way as in the case of FIGS. 1–3, when said two components were merely mixed and when they were fired.

FIG. 13 shows the CO removal rate, FIG. 4 shows the NO formation rate, and FIG. 15 shows the N$_2$ formation rate.

FIG. 16 shows the effect of the addition of Pd or Pt on sensor sensitivity by testing the sensors using said materials.

BEST MODE FOR CARRYING OUT THE INVENTION

The present invention is described below with reference to the embodiments thereof.

EXAMPLE 1

SrTiO$_3$ was mixed in the ratios of 0, 20, 40, 60 and 80% by mole in Sr$_{0.65}$La$_{0.35}$Co$_{0.7}$Fe$_{0.3}$O$_{3-\delta}$ prepared according to the method of U.S. Pat. No. 4,314,996, and each mixture was fired in the air at 1,3000° C. for 3 hours and then pulverized to 325 meshes. 0.3 g of the pulverized material was picked up, supported on 0.4 g of alumina-silica fiber and packed in the center of a quartz glass tube. It was heated to a predetermined temperature by a tubular electric furnace, and a gaseous mixture consisting of 40 ppm of NO$_2$, 150 ppm of CO and the balancing quantity of nitrogen was supplied into the tube from its inlet at a space velocity of 8,000h$^{-1}$, and the CO, NO$_2$ and NO$_x$ concentrations at the outlet were measured, from which the CO removal rate, NO formation rate and N$_2$ formation rate were determined. $\delta$ denotes the loss of oxygen.

Figure 1:
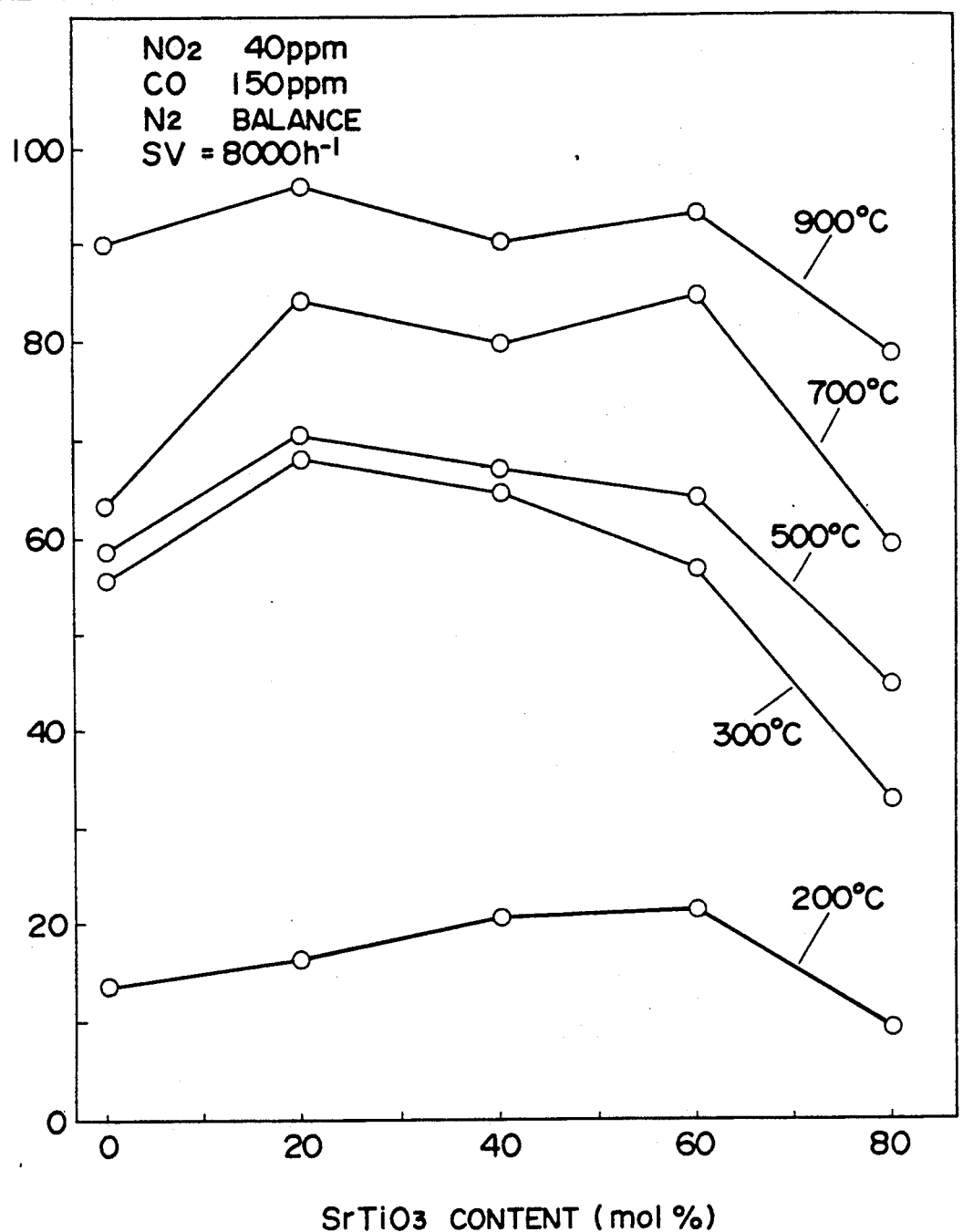
FIGS. 1 to 3 show the catalytic effect for cleaning gas when a mixed gas consisting of 40 ppm of NO$_2$, 150 ppm of CO and the remaining portion of nitrogen was passed through a sintered specimen of catalyst composition comprising Sr$_{0.65}$La$_{0.35}$Co$_{0.7}$Fe$_{0.3}$O$_{3-\delta}$ and SrTiO$_3$. In these figures.
Figure 2:
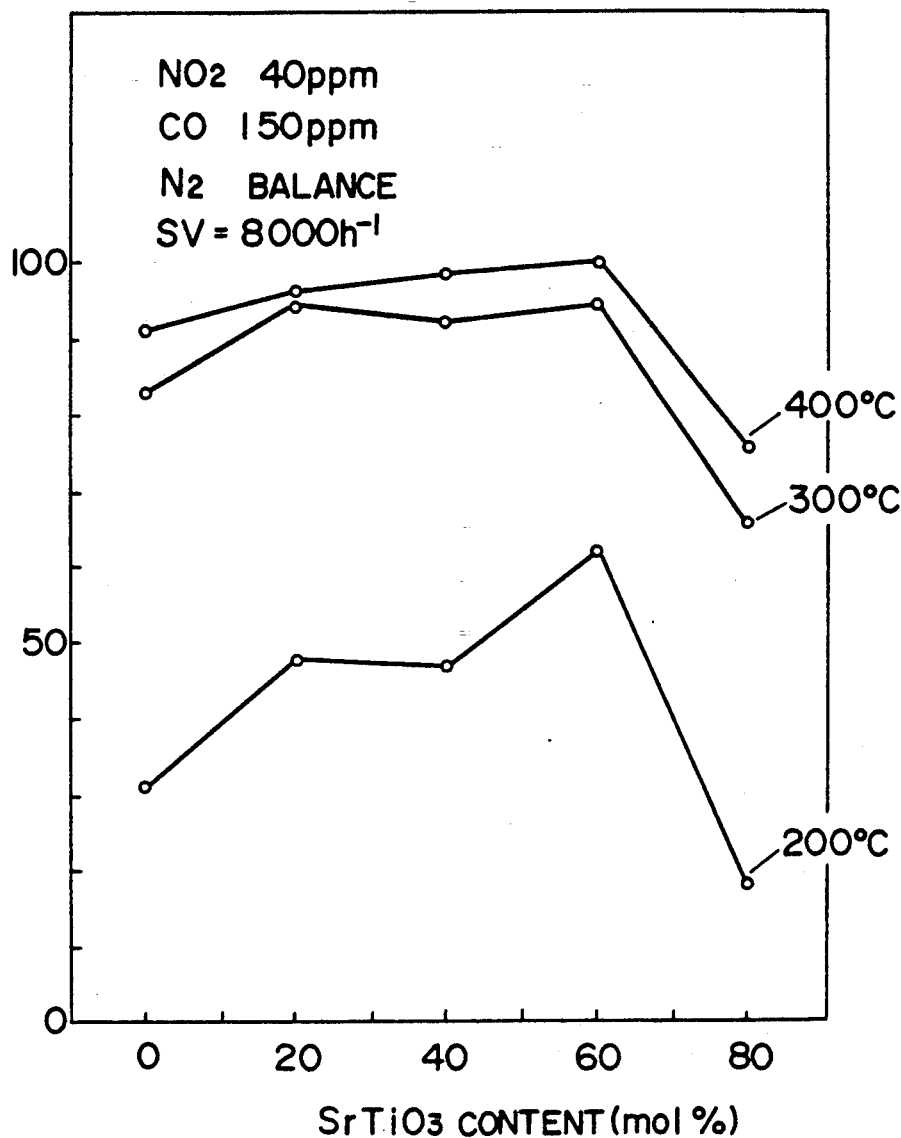
Figure 3:
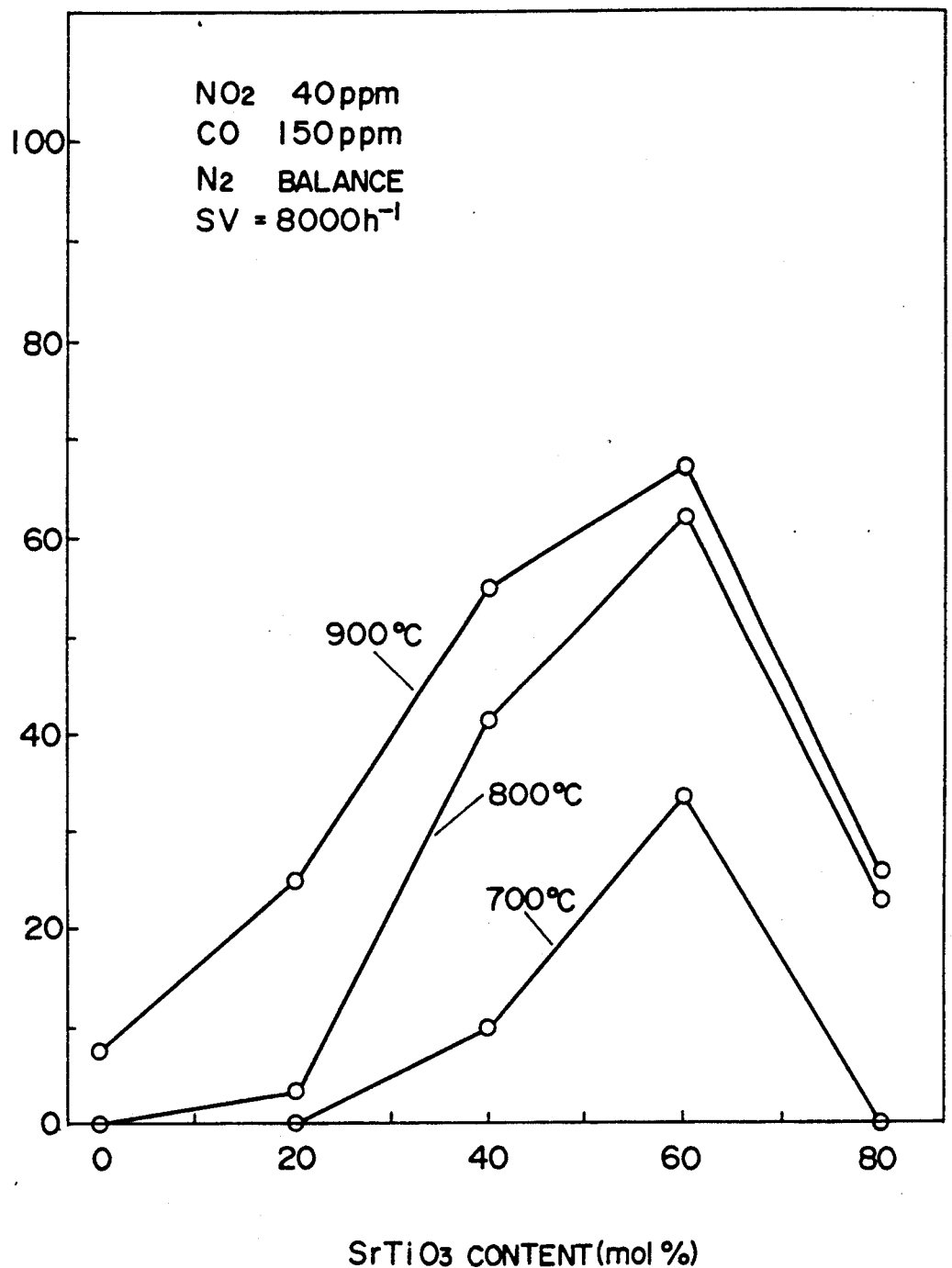

These rates of change were as shown in FIGS. 1–3. The CO removal rate became the highest when the amount of SrTiO$_3$ added was 20–60% by mole, and in this region an increase of activity by the addition of SrTiO$_3$ was seen. Also, there were seen a peak of NO formation rate at low temperature and a peak of N$_2$ formation rate at high temperature at SrTiO$_3$ content of 60 mol %. Viewing generally, a marked improvement of catalytic cleaning performance was seen by the addition of 60 mol % of SrTiO$_3$.

EXAMPLE 2

In order to see the influence of dispersion of SrTiO$_3$, there were prepared two samples in one of which SrTiO$_3$ was merely mixed and in the other sample the mixture was further fired at 1,300° C. for 3 hours, both samples containing 60 mol % of SrTiO$_3$ which content gave high catalytic performance in Example 1. These samples were subjected to a comparative test for catalytic performance in the same way as in Example 1, and the results were shown in terms of CO removal rate, NO formation rate and N₂ formation rate in FIGS. 4–6.

The fired mixture showed a higher catalystic cleaning effect than the simple mixture in each case, but the difference was slight. It was noted that the addition of $SrTiO_3$ accounts for a substantial portion of the effect.

EXAMPLE 3

In order to see the effect of the addition of $SrTiO_3$ on catalyst life, $SrTiO_3$ was added in a ratio of 60 mol % to $Sr_{0.65}La_{0.35}Co_{0.7}Me_{0.3}O_{3-\delta}$ (Me: Fe, Mn, Cr or V), followed by firing to prepare the fired mixtures. There were also prepared the samples with no $SrTiO_3$ added and merely comprising $Sr_{0.65}La_{0.35}Co_{0.7}Me_{0.3}O_{3-\delta}$ where Me was Fe or Mn. Each sample was supported on alumina-silica fiber, set at the top (exhaust gas temperature: about 850° C.) of the combustion cylinder of a marketed portable stove and subjected to 1,000 times of repetition of one-hour burning -15-minute extinction cycle. The effect on life was determined from the change of values of CO removal rate, NO formation rate and N₂ formation rate measured in the same way as in Example 1 before and after each said cycle.

Figure 9:
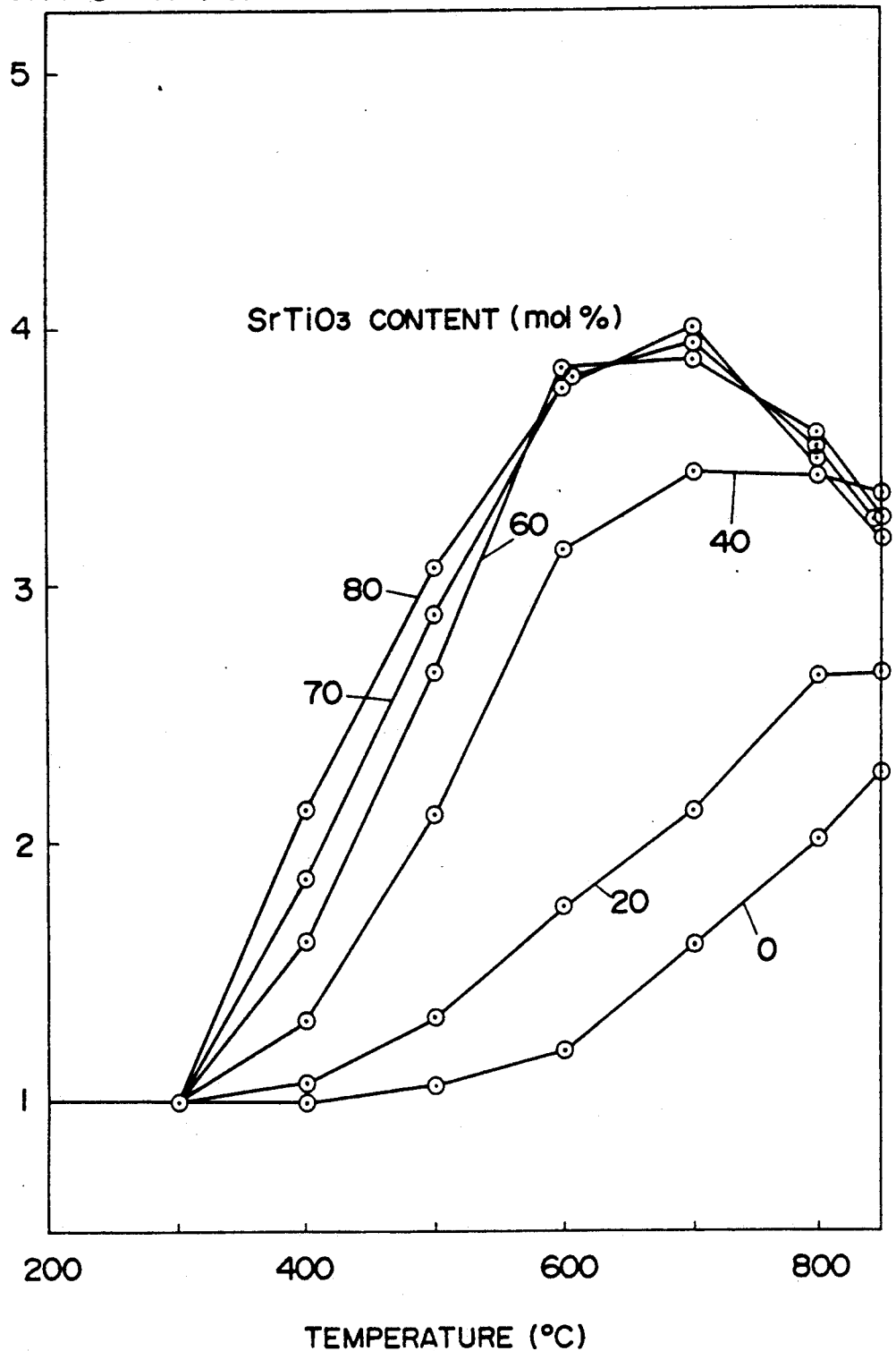
FIG. 9 shows the effect of the addition of SrTiO$_3$ on sensor sensitivity in terms of the ratio of electric resistance 15 minutes after conversion to 10 ppm CO to the stationary electric resistance in the air (at various temperatures).
Figure 10:
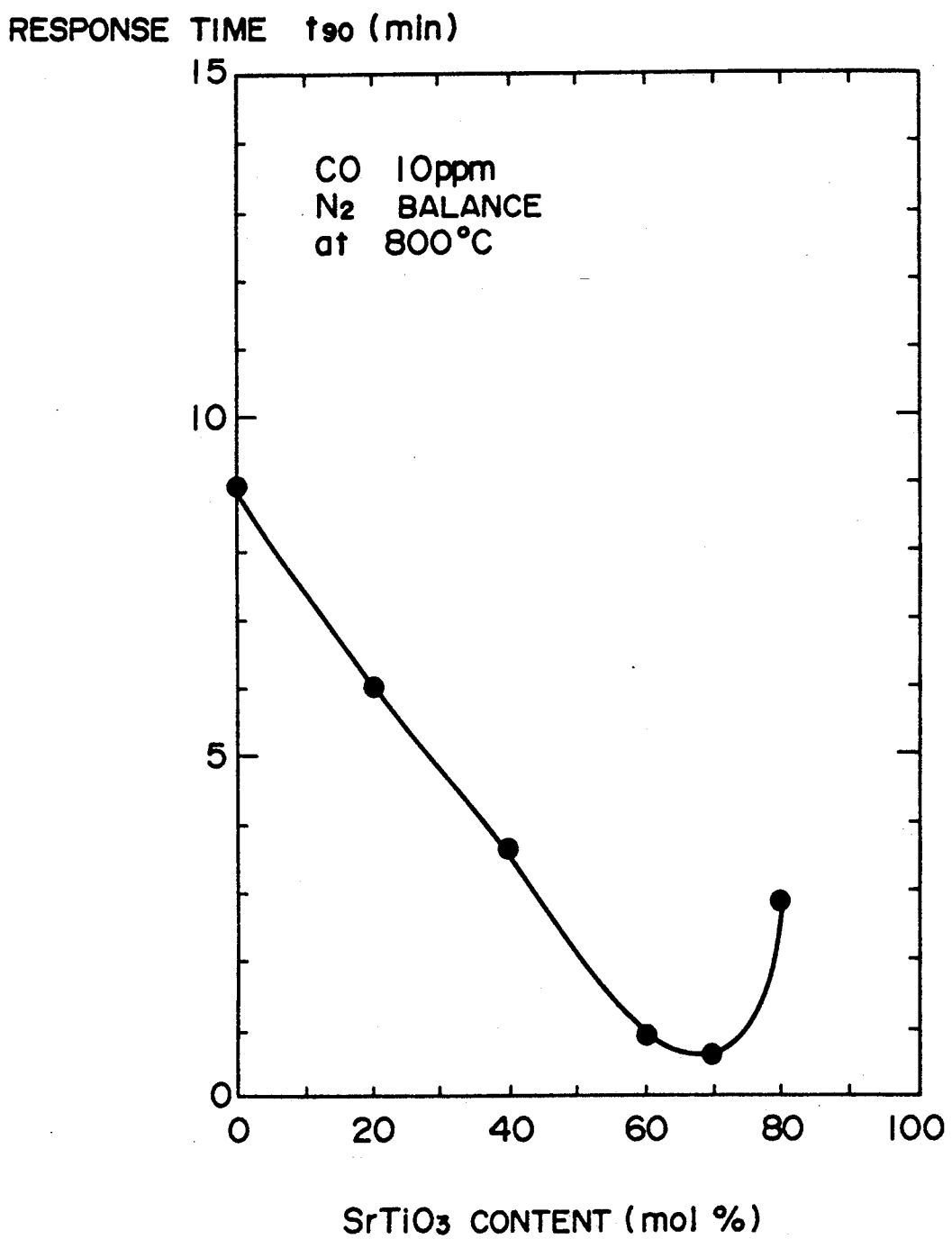
FIG. 10 shows the effect of the addition of SrTiO$_3$ on sensor responsiveness in terms of the span of time in which 90% of electric resistance after the passage of 15 minutes can be obtained.

The measured values were as shown in Table 1, and it was considered that the addition of $SrTiO_3$ was conductive to the enhancement of catalytic performance and the prolongation of catalyst life, regardless of the type of substituting element at the B site.

various temperatures, and the results were shown in terms of stationary resistivity in the air, sensitivity S (resistivity ($R_G$) 15 minutes after conversion to CO/stationary resistivity ($R_A$) in the air), and response time at 800° C. (time in which 80% of the change of resistance during 15 minutes after CO conversion), in FIG. 8, FIG. 9 and FIG. 10, respectively.

Figure 8:
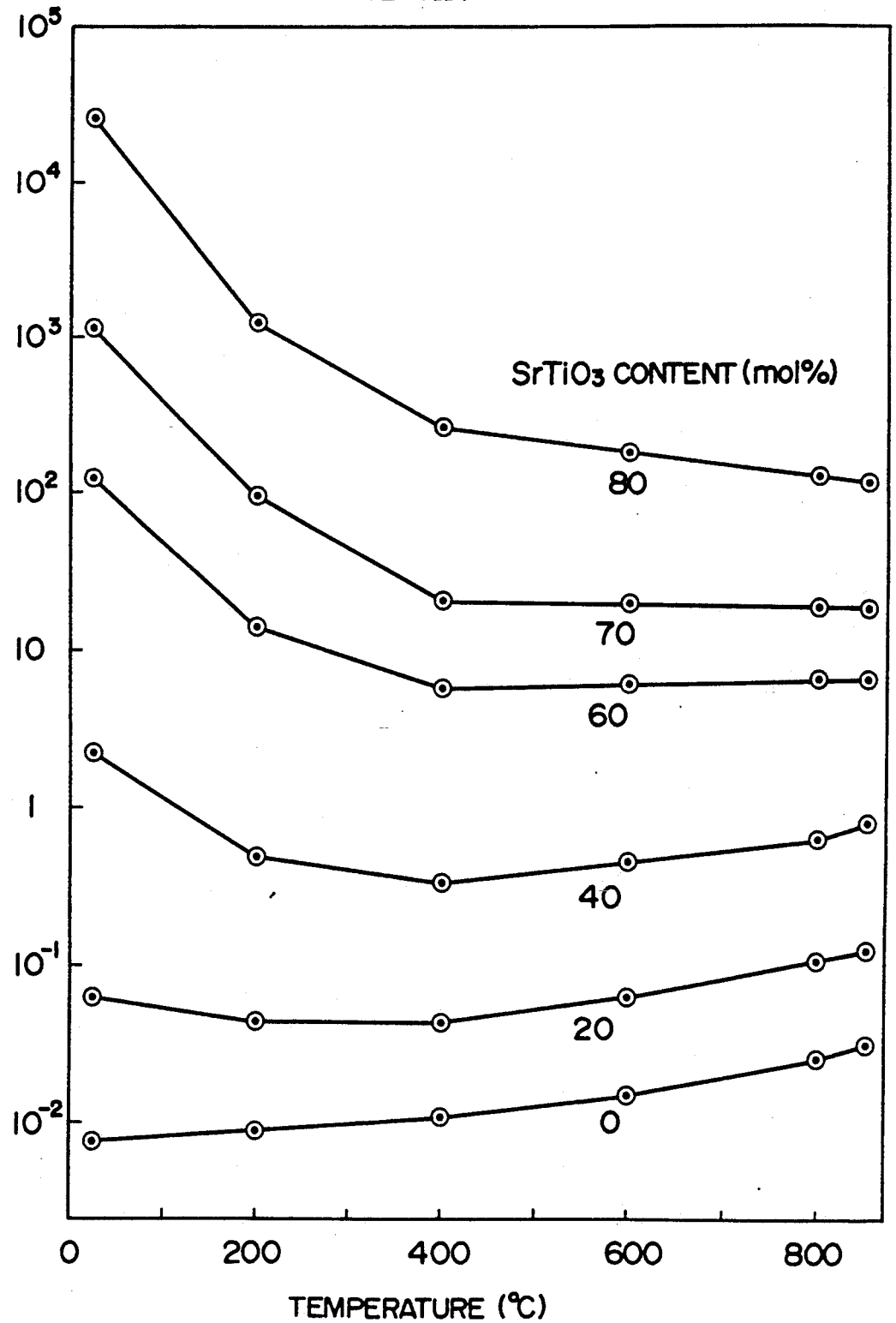
FIG. 8 shows the change by temperature of the resistance in air of the sintered type sensor made by adding SrTiO$_3$ to Sr$_{0.65}$La$_{0.35}$Co$_{0.7}$Fe$_{0.3}$O$_{3-\delta}$.

It is seen from FIG. 8 that in the sensor elements to which no $SrTiO_3$ was added, the change of resistance in the air according to temperature resembles the metallic pattern of change, but when $SrTiO_3$ is added, a semiconductor type change occurs in the low temperature region, and at around 60–70 mol % there comes out a zone where no change of resistance occurs in the temperature range capable of maintaining gas sensitivity. This phenomenon can be utilized for a temperature sensor to be used for the detection of firing and going-out of fire or the detection of a fire, and when it is utilized as a sensor for detecting the stoichiometric composition of combustion, there is provided the advantage of eliminating the temperature compensation usually required in the sensors using $TiO_2$ or $SnO_2$. It is noted from FIGS. 9 and 10 that in use of the product as a sensor for detecting the stoichiometric composition, the addition of $SrTiO_3$ in said amount range gives the highest effect for the increase of sensitivity and responsiveness.

TABLE 1

| | CO removal rate (%) | | NO formation rate (%) | | N₂ formation rate (%) | |
|---|---|---|---|---|---|---|
| | Initial | After test | Initial | After test | Initial | After test |
| $Sr_{0.65}La_{0.35}Co_{0.7}Me_{0.3}O_{3-\delta}$ 40 mol % (Me=Fe) $SrTiO_3$ 60 mol % | 64.5 | 63.5 | 94.5 | 93.0 | 69.0 | 66.5 |
| $Sr_{0.65}La_{0.35}Co_{0.7}Me_{0.3}O_{3-\delta}$ 40 mol % (Me=Mn) $SrTiO_3$ 60 mol % | 63.0 | 61.5 | 93.0 | 91.0 | 66.5 | 64.0 |
| $Sr_{0.65}La_{0.35}Co_{0.7}Me_{0.3}O_{3-\delta}$ 40 mol % (Me=Cr) $SrTiO_3$ 60 mol % | 63.0 | 61.0 | 92.5 | 90.5 | 67.0 | 63.5 |
| $Sr_{0.65}La_{0.35}Co_{0.7}Me_{0.3}O_{3-\delta}$ 40 mol % (Me=V) $SrTiO_3$ 60 mol % | 62.0 | 59.5 | 90.5 | 86.5 | 63.5 | 60.5 |
| $Sr_{0.65}La_{0.35}Co_{0.7}Fe_{0.3}O_{3-\delta}$ | 52.0 | 46.5 | 83.0 | 78.5 | 7.0 | 4.0 |
| $Sr_{0.65}La_{0.35}Co_{0.7}Mn_{0.3}O_{3-\delta}$ | 50.5 | 43.0 | 79.5 | 75.0 | 5.5 | 2.5 |

EXAMPLE 4

Figure 7A:
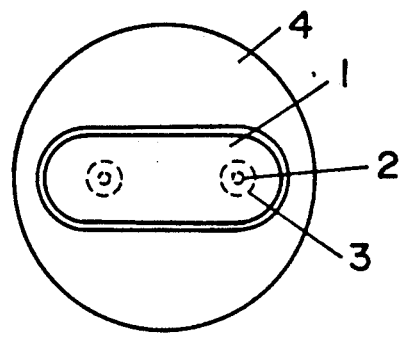
FIG. 7 (a), (b) and (c) are the schematic drawings illustrating the structure of a sintered type sensor made by adding SrTiO$_3$ to Sr$_{0.65}$La$_{0.35}$Co$_{0.7}$Fe$_{0.3}$O$_{3-\delta}$.
Figure 7B:
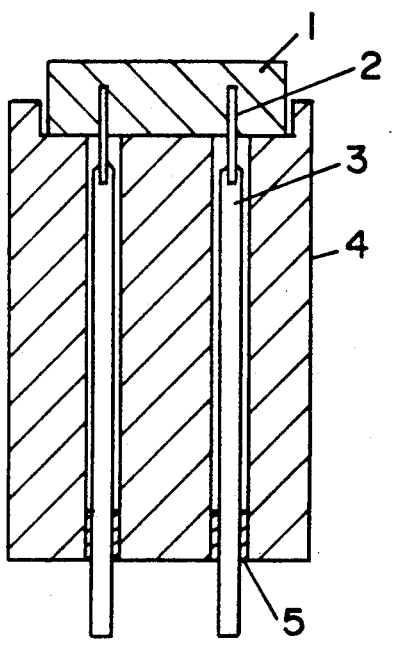
Figure 7C:
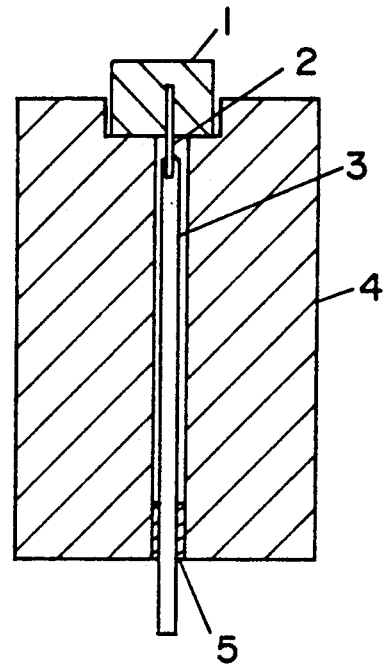

To $Sr_{0.65}La_{0.35}Co_{0.7}Fe_{0.3}O_{3-\delta}$ were added $SrTiO_3$ in amounts of 20, 40, 60, 70 and 80% by mole and carboxymethyl cellulose in an amount of 20% by weight (outer percentage), and each mixture was press molded under a pressure of 1 t/cm² and fired at 1,350° C. for 3 hours to make a sensor element. The sintered sensor element had a structure shown in FIG. 7. A Pd(0.8)-Ag(0.2) alloy was connected as electrode lead 2, with its end embedded in sensor base 1, and heat-resistant metal lead 3 was secured to said electrode lead 2 and fixed to ceramic tube 4 by fixing means 5. FIG. 7(a) is a top plan view of the sensor, and (b) and (c) are sectional views of the different sides. The resistance of this sensor in the air and the resistance thereof 15 minutes after conversion of the atmosphere to 10 ppm CO/N₂ were measured at

EXAMPLE 5

To $Sr_{0.65}La_{0.35}Co_{0.7}Fe_{0.3}O_{3-\delta}$ were severally added $SrTiO_3$, $SrZrO_3$, $SrHfO_3$, and 30: 60 and 60: 90 mixtures of $SrTiO_3$ and $SrZrO_3$, each in an amount of 60% by mole, and each mixture was molded and fired at 1,350° C. for 2 hours. The electric resistance of the product in the air and the electric resistance thereof 30 seconds after (atmospheric) conversion to 100 ppm CO/N₂ were measured at temperatures 200° C. apart from each other, starting from room temperature.

Figure 11:
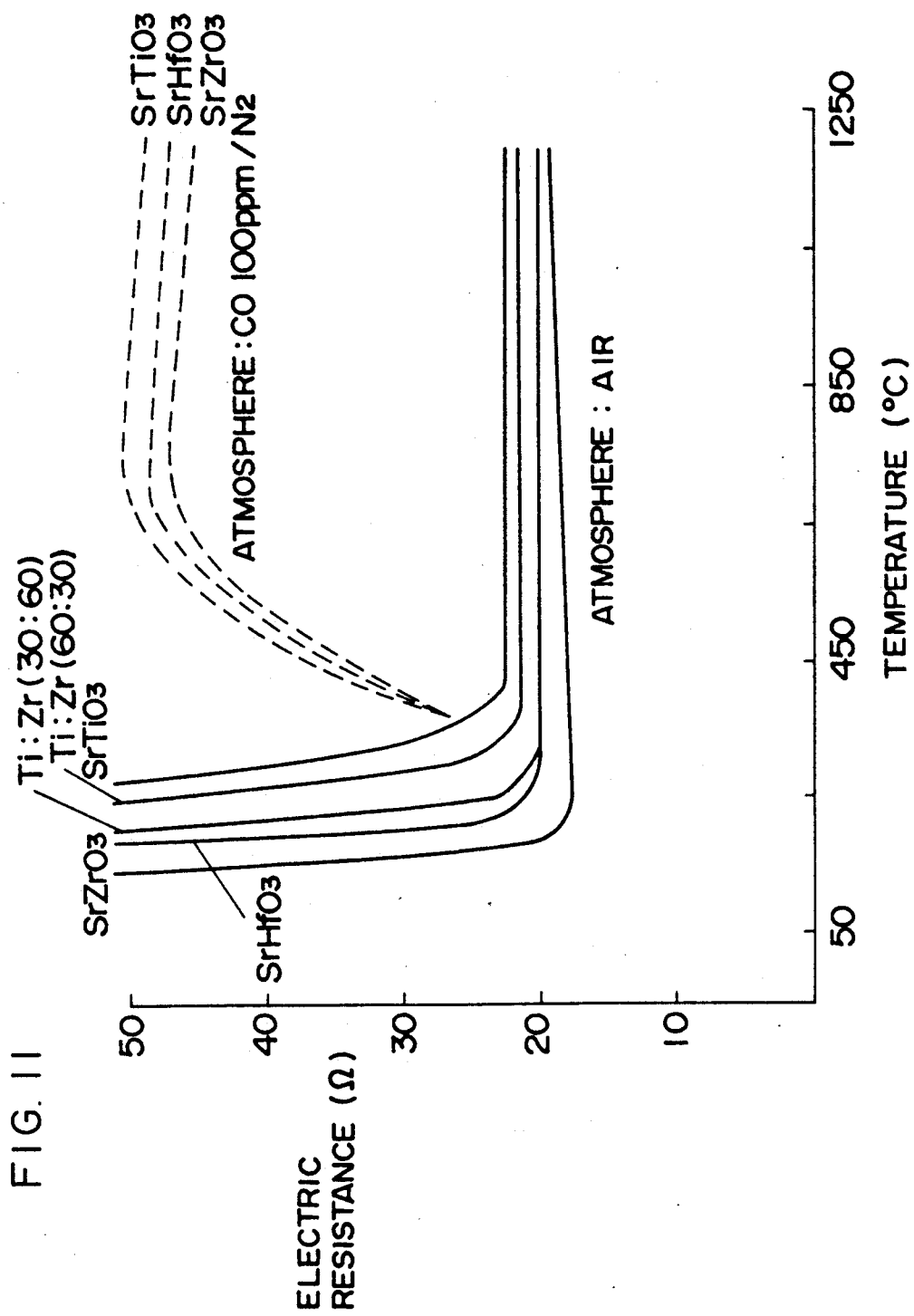
FIG. 11 shows the electric resistance at various temperatures of the sintered elements in which the grain boundary forming agents other than SrTiO$_3$ were added in a ratio of 60 mol % to Sr$_{0.65}$La$_{0.35}$Co$_{0.7}$Fe$_{0.3}$O$_{3-\delta}$ as determined in the air and in the atmosphere of 100 ppm CO (one minute after conversion).

FIG. 11 shows the measured values of electric resistance. As evident from the graph, if a second material such as $SrTiO_3$, $SrZrO_3$, etc., is added in a proper amount (45–70% by mole), there can be obtained a product which shows high electric resistance in the low temperature region and shows no change of electric resistance in the air in the high temperature region where the detection of stoichiometric composition is possible. (However, the proper amount differs slightly from one material to the other). The critical temperature differs depending on the type of the material added; it is around 400° C. in the case of $SrTiO_3$, around 200° C. in the case of $SrZrO_3$ and around 250° C. in the case of $SrHfO_3$. Mixing of a second material also makes it possible to select an intermediate critical temperature.

Thus, by the addition of a second material, it is possible to change the critical temperature in the low temperature region according to the type of the second material but the sensor characteristics are unchanged to any significant degree, and in each case a high sensitivity and high responsiveness are provided in comparison with the products to which no second material was added.

EXAMPLE 6

Figure 12:
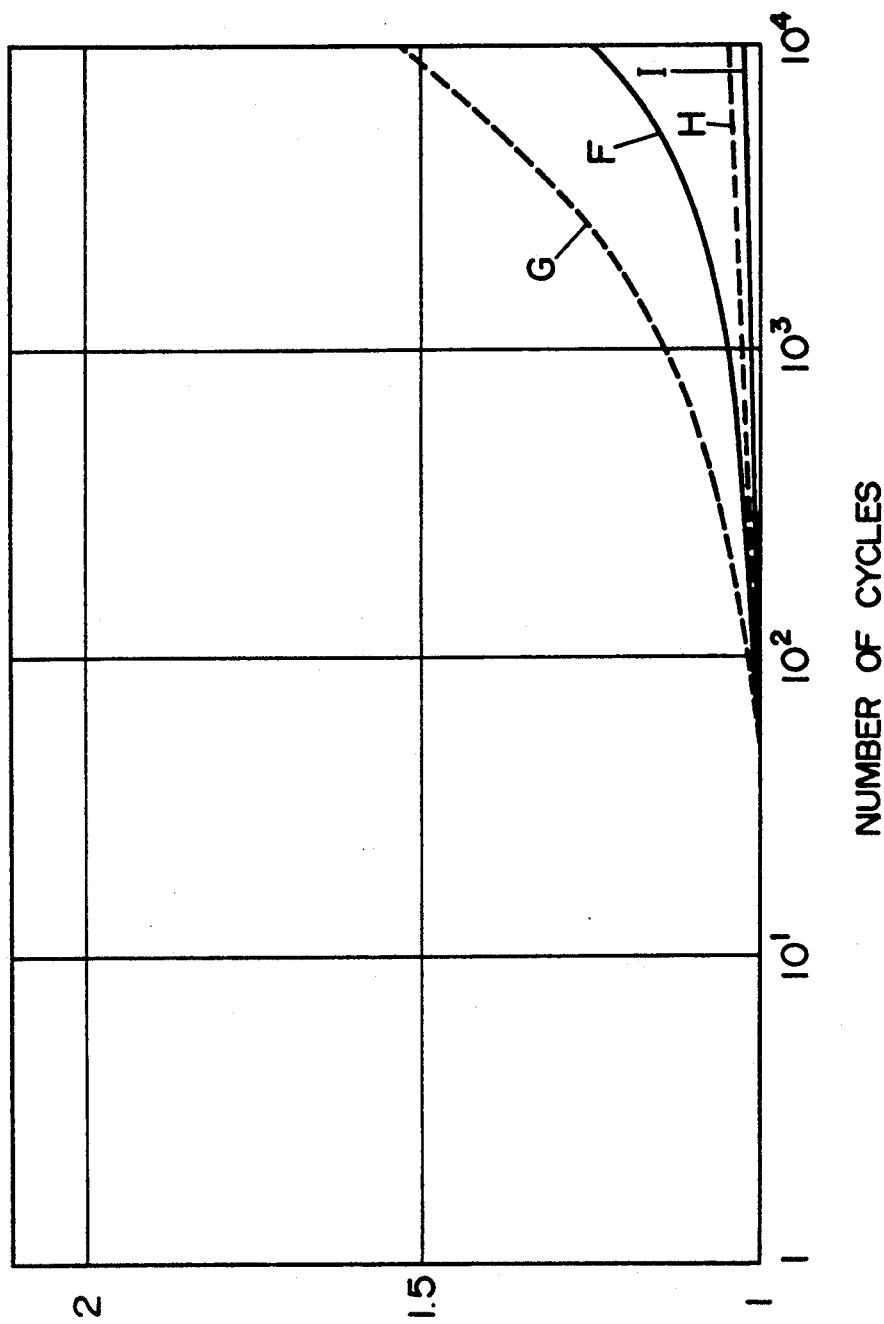
FIG. 12 shows the influence of the addition of SrTiO$_3$ on sensor life by measuring the change of resistance of the sensors with compositions of Sr$_{0.5}$La$_{0.5}$CoO$_{3-\delta}$ and Sr$_{0.65}$La$_{0.35}$Co$_{0.7}$Fe$_{0.3}$O$_{3-\delta}$ with no addition of SrTiO$_3$ or added with 60 mol % of SrTiO$_3$.

In order to see the effect of the addition of $SrTiO_3$ on sensor life, there were prepared the sensors in which $SrTiO_3$ was added in an amount of 60% by mole to $Sr_{0.5}La_{0.5}CoO_{3-\delta}$ and $Sr_{0.65}La_{0.35}Co_{0.7}Fe_{0.3}O_{3-\delta}$ and those in which no $SrTiO_3$ was added. Air was passed through each product at a flow rate of 1 l/min at 800° C. for 5 minutes and then 100 ppm $CO/N_2$ was passed under the same conditions for one minute, the sensor being cooled to room temperature at the end of every 60 cycles. The change of stationary electric resistance in the air as observed in the repetition of said cycles was shown in FIG. 12. The sensor production method was the same as in Example 4.

It is seen that the addition of $SrTiO_3$ noticeably prolongs the sensor life regardless of the kind of $Sr_{(1+x)/2}La_{(1-x)/2}Co_{1-x}Fe_xO_{3-\delta}$. This is considered attributable to the fact that the thermal expansion coefficient of the sensor element approaches that $(13-14\times10^{-6}\ deg^{-1})$ of the electrode lead material by the addition of $SrTiO_3$ as shown in Table 2.

TABLE 2

| Samples | Composition | Thermal expansion coefficient ($\times 10^{-6}$/deg.) |
| --- | --- | --- |
| F | $Sr_{0.5}La_{0.5}CoO_{3-\delta}$ | 19.4 |
| G | $Sr_{0.65}La_{0.35}Co_{0.7}Fe_{0.3}O_{3-\delta}$ | 22.6 |
| H | F + $SrTiO_3$ (60 mol %) | 16.2 |
| I | G + $SrTiO_3$ (60 mol %) | 13.7 |

EXAMPLE 7

Figure 13:
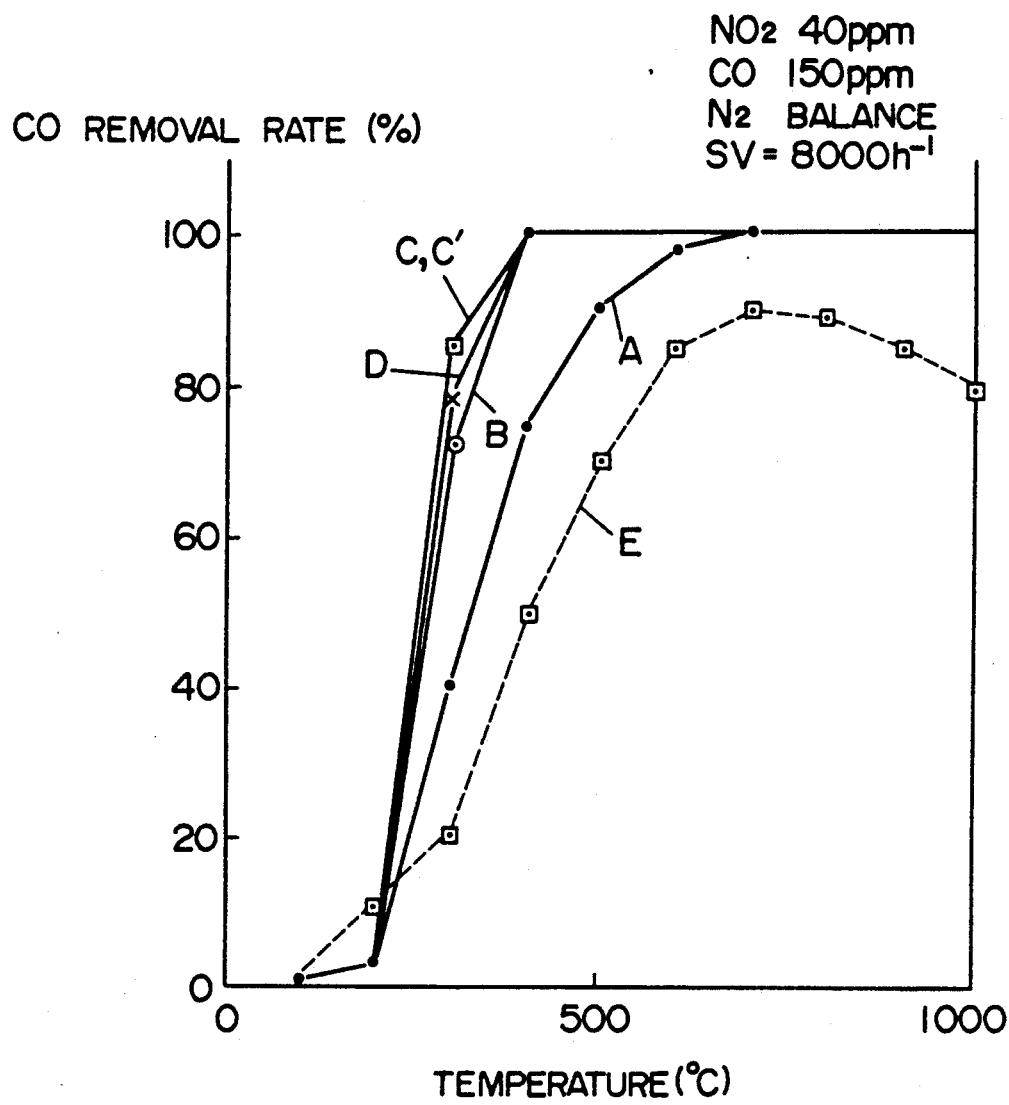
FIGS. 13–15 show the exhaust gas cleaning effect in the case when Pd or Pt was further added to the specimens comprising Sr$_{0.65}$La$_{0.35}$Co$_{0.7}$Fe$_{0.3}$O$_{3-\delta}$ and SrTiO$_3$. In these figures.
Figure 14:
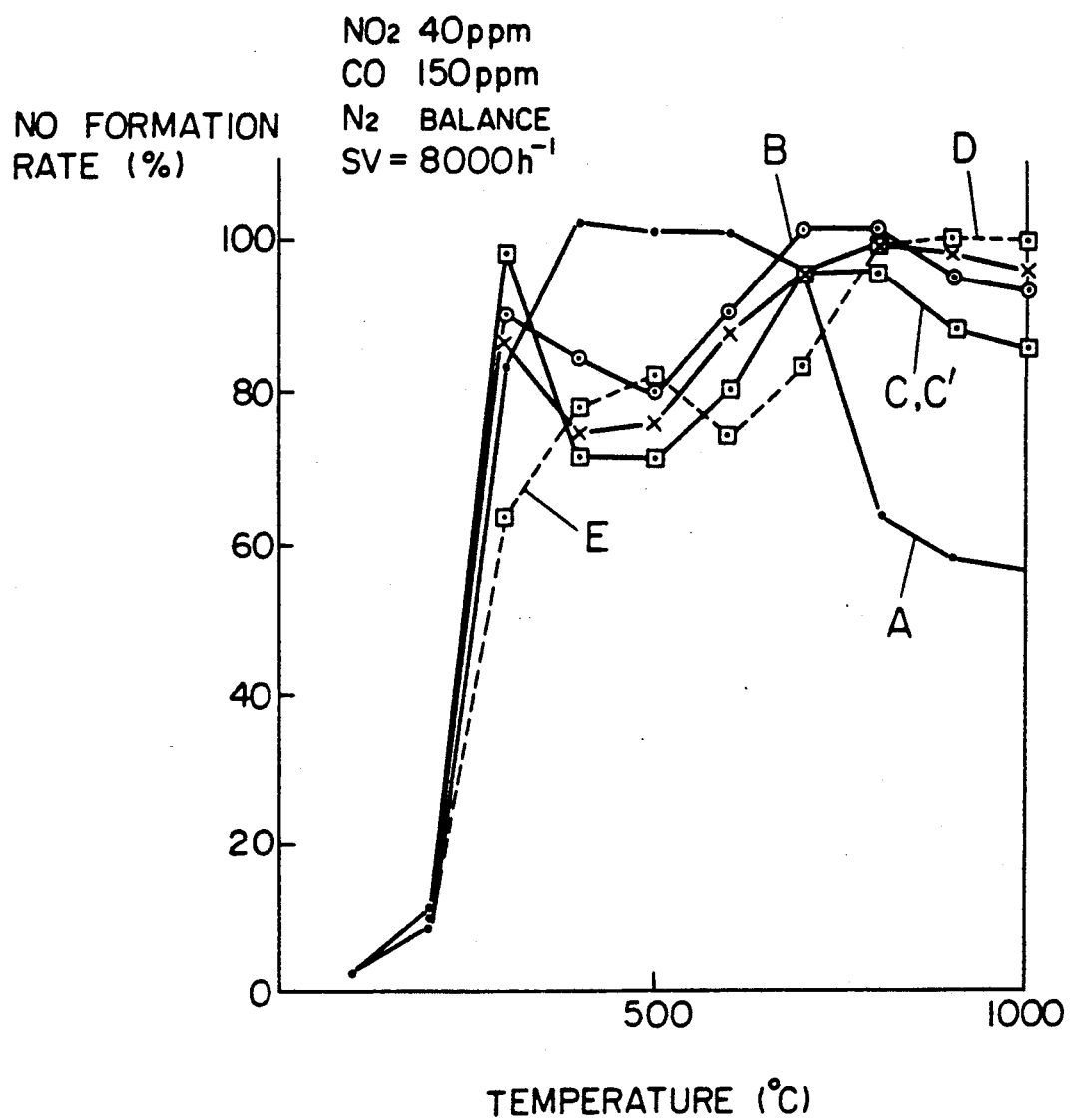
Figure 15:
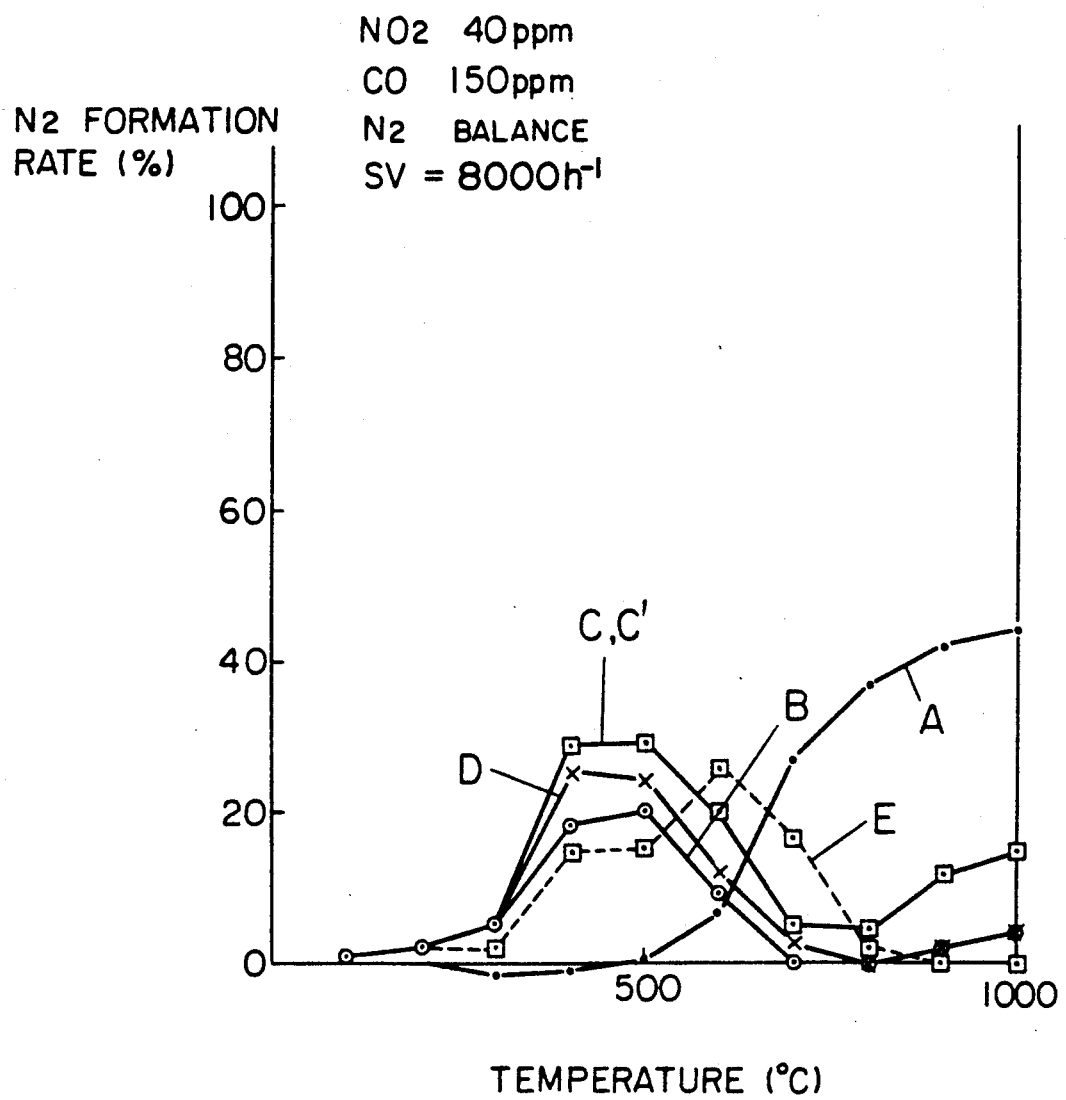

In order to see the effect produced on catalytic performance and sensor sensitivity by the addition of Pd or Pt in addition to the grain boundary forming agent $SrMéO_3$ (Mé: Ti, Zr or Hf) shown in Examples 1–6, mixtures were prepared by adding Pd in amounts of 0, 0.3, 0.6 and 0.9% by weight and Pt in an amount of 0.6% by weight to the mixture made by adding $SrTiO_3$ powder in a ratio of 65% by mole to $Sr_{0.65}La_{0.35}Co_{0.7}Fe_{0.3}O_{3-\delta}$ powder. Each of these mixtures was molded, fired at 1,200° C. for 3 hours, pulverized and supported on silica-alumina fiber in the same way as in Example 1 to determine the catalytic performance. In this experiment, for the purpose of comparison, there were also prepared a sample in which the same amount (equivalent to 0.3% by weight) of Pt alone was supported. These samples are shown in Table 3. The noxious gas cleaning effect at various temperatures was as shown in FIGS. 13–15.

TABLE 3

| Samples | $Sr_{0.65}La_{0.35}Co_{0.7}Fe_{0.3}O_{3-\delta}$ | $SrTiO_3$ | Pd | Pt |
| --- | --- | --- | --- | --- |
| A | 35 mol % | 63 mol % | — | — |
| B | 35 | 65 | 0.3 wt % | — |
| C | 35 | 65 | 0.6 wt % | — |
| C' | 35 | 65 | — | 0.6 wt % |
| D | 35 | 65 | 0.9 wt % | — |
| E | Pt alone (equivalent to 0.3% by weight) | | | |

It is seen that the addition of Pd or Pt improves the cleaning performance in the low temperature region. It is also noted that the combined use of Pt with the mixture of $Sr_{0.65}La_{0.35}Co_{0.7}Fe_{0.3}O_{3-\delta}$ and $SrTiO_3$ can improve the catalytic performance more than when Pt alone is used.

Also, sensor samples were made by using said mixtures in the same way as in Example 4 except that the firing temperature was changed to 1,200° C., and the determination of their sensitivity was conducted. The determined values of sensitivity were as shown in FIG. 16, from which it is seen that the gas sensitivity is improved as is the catalytic performance especially in the low temperature region by the addition of Pd or Pt.

The improvement of catalytic performance and sensor characteristics in the low temperature region may be accounted for by the fact that the migration of oxygen ions in the base is regulated by the transfer of charges in the base surface at low temperatures and decelerated, but the transfer of charges is promoted by the addition of Pd or Pt to accelerate the ionic migration.

EXAMPLE 8

Figure 17A:
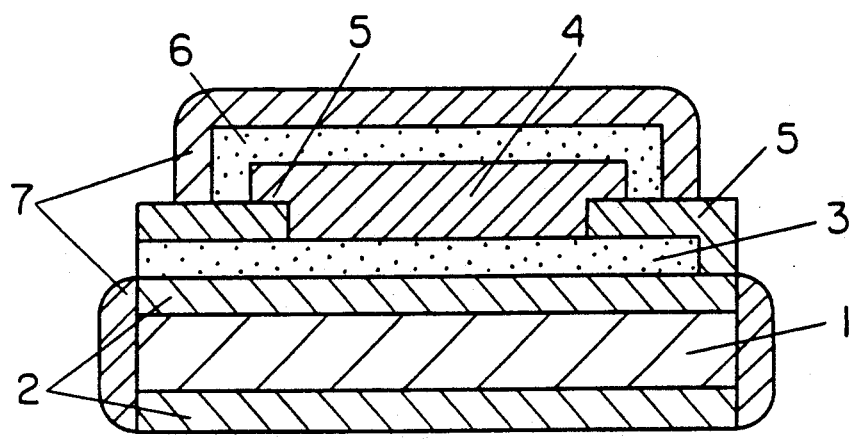
FIG. 17(a) and (b) are the schematic drawings illustrating the structure of a sensor for detecting the air/fuel ratio other than the stoichiometric composition by combining said stoichiometric composition sensor and a zirconia oxygen pump.
Figure 17B:
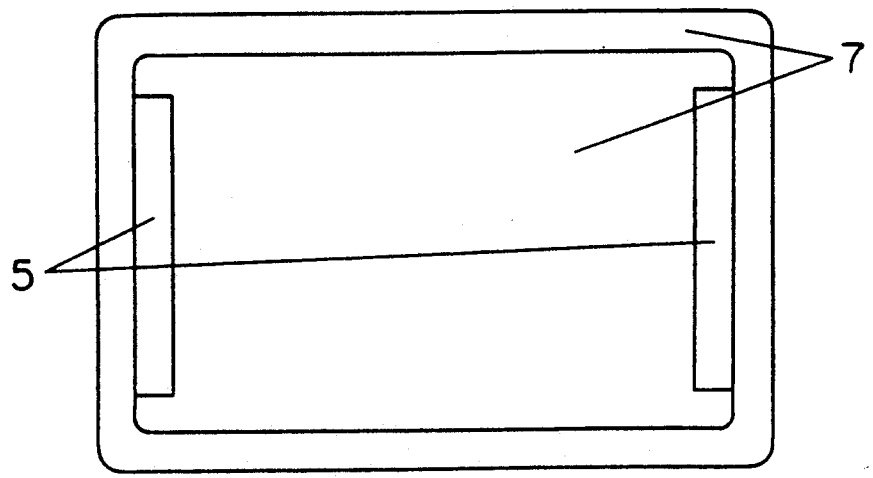

The sensor of equivalent composition of combustion of Example 7, adapted as a detector, was combined with a zirconia oxygen pump to make a sensor for detecting the air/fuel ratio other than the equivalent composition shown in FIG. 17. In the drawings of FIG. 17, numeral 1 denotes a zirconia electrolyte plate stabilized by adding 8% by mole of $Y_2O_3$, 2 the electrodes formed by baking the oxygen pump-forming Pt paste at 900° C. for 30 minutes on said electrolyte plate 1, 3 an $SrTiO_3$ layer screen printed on one said electrodes, and 4 a sensor for detecting the equivalent composition, which was screen printed on said $SrTiO_3$ layer. In this example, $SrTiO_3$ was added in amounts of 30, 60 and 80% by mole to $Sr_{0.575}La_{0.425}Co_{0.85}Fe_{0.15}O_{3-\delta}$, and in the case of 3, butylcarbitol acetate and α-terpineol were added each in a rate of 10% to prepare printing ink. 5 indicates two electrodes of sensor 4, which were made with the same material and by the same process as sensor 2. 6 is a $SrTiO_3$ layer which is the same as 3 and was screen printed. 7 is a gas-impermeable glass coat. The thus produced sensor was set at the center of a tubular electric furnace. It was maintained at 800° C. while the atmospheric oxygen concentration was kept constant at 2%, and by changing the current values of the oxygen pump in a condition where the CO concentration was changed to 0, 1, 2 and 4% (the rest being $N_2$), the current inducing a sharp change of electric resistance of the detector was determined.

Figure 18:
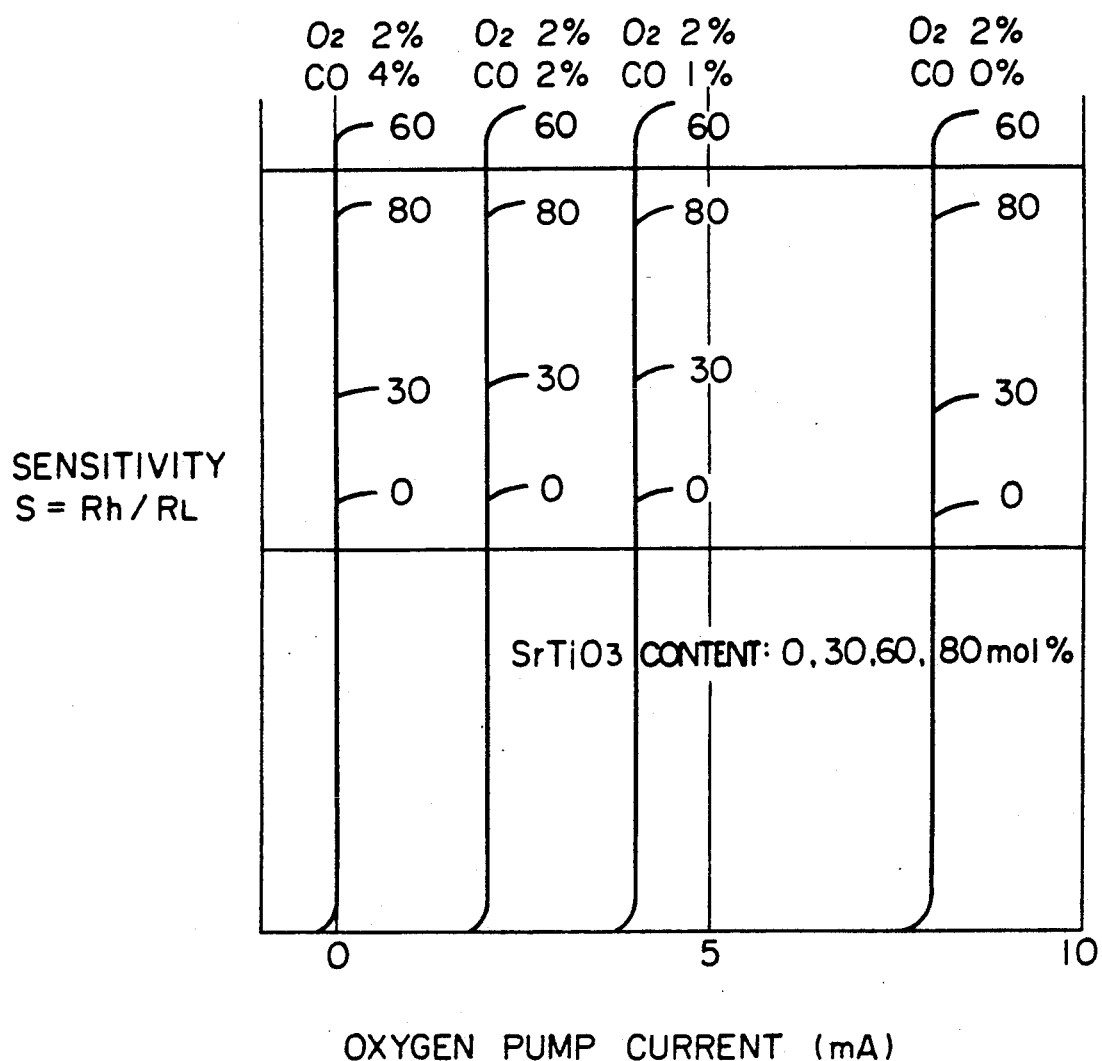
FIG. 18 is a diagram showing the relation between pump current and change of resistance according to the atmospheric gas composition of said sensors using an stoichiometric composition sensor made by a screen printing method by adding SrTiO$_3$ to Sr$_{0.575}$La$_{0.425}$Co$_{0.85}$Fe$_{0.15}$O$_{3-\delta}$.

The determinations were as shown in FIG. 18, from which it is seen that the electric resistance of the detector is changed sharply when a pump current corresponding to excess oxygen is flown regardless of the content of $SrTiO_3$. This means that if the current of the oxygen pump is set to a proper value, it is possible to detect the air/fuel ratio other than the stoichiometric composition from the sudden change of electric resistance. In this case, since the detector merely undergoes a sudden change of resistance at a point where its surrounding gas reached the stoichiometric composition, the detector sensitivity is naturally high at the $SrTiO_3$ content of around 60 mol %. Although no data were shown about life, it is considered that the life is also long in this area of composition.

It was also found that the sensors using a ceramic substrate mainly composed of strontium titanate, as compared with those using an alumina type or silica type ceramic substrate, are limited (less than 5%) in change of electric resistance even in the tests of 5,000 cycles and were improved in life.

The compositions in said examples may be a mixture or a fired product of $Sr_{(1+x)/2}La_{(1-x)/2}Co_{1-x}Me_xO_{3-\delta}$ and $SrMéO_3$, and the detector product may be one obtained by sintering the molded material like ordinary ceramics or by flame-spraying the powdery mixture or by heating and sintering the mixture after screen printing.

INDUSTRIAL APPLICABILITY

As described above, in accordance with this invention, by adding $SrMéO_3$ (Mé: Ti, Zr or Hf) to $Sr_{(1+x)/2}La_{(1-x)/2}Co_{1-x}Me_xO_{3-\delta}$ (Me: Fe, Mn, Cr or V δ: loss of oxygen) of the prior invention, the $O^2$ ion transference number is increased $10^3$-$10^4$ times over when no $SrMéO_3$ is added, thus enabling not only an improvement of catalytic cleaning performance for exhaust gas from combustors or internal combustion engines and of sensor sensitivity and responsiveness for detecting the stoichiometric composition of exhaust gas, but also multiplication of temperature detecting functions without semiconductor type temperature dependency in the low temperature region and without temperature dependency in use in the air in the high temperature region (above 400° C.). Thus, the present invention is capable of providing a sensor having no necessity of temperature compensation and useful for the prevention of danger and for the control of low fuel cost. Also, the addition of said material ($SrMéO_3$) is helpful for reducing the thermal expansion coefficient to make the combined use with other materials easy. This facilitates the combination of a sensor for detecting the stoichiometric composition and an oxygen pump and enables application to sensors for detecting air/fuel ratio other than the stoichiometric composition. The catalytic performance and sensor characteristics at low temperatures can be improved by the addition of a third component such as Pd or Pt.

What is claimed is:

1. A composition consisting essentially of a mixture of $Sr_{(1+x)/2}La_{(1-x)/2}Co_{1-x}Me_xO_{3-\delta}$ wherein $0 < x \leq 1$; δ represents loss of oxygen, and Me is at least one of Fe, Mn, Cr and V;

and $SrMéO_3$, wherein Mé is at least one of Ti, Zr and Hf.

2. A composition of claim 1 wherein the amount of said $SrMéO_3$ is 60–70% by mole.

3. A composition of claim 1 wherein x in the general formula is defined as $0 \leq x \leq 0.3$.

4. A composition of claim 1, wherein the mixture is fired.

5. A multi-functional sensor using as an electric resistance element a composition consisting essentially of $Sr_{(1+x)/2}La_{(1-x)/2}Co_{1-x}Me_xO_{3-\delta}$ wherein $0 < x \leq 1$; δ represents loss of oxygen; and Me is at least one of Fe, Mn, Cr and V;

and $SrMéO_3$, wherein Mé is at least one of Ti, Zr and Hf;

said sensor being adapted for detecting combustion, cessation of combustion and the stoichiometric composition of combustion according to the change in electric resistance of said electric resistance element.

6. A multi-functional sensor according to claim 5, wherein x in the general formula is defined as $0 \leq x \leq 0.3$.

7. A multi-functional sensor according to claim 5, wherein the amount of said $SrMéO_3$ is 60–70% by mole.

8. A multi-functional sensor according to claim 5, wherein an oxygen pump is combined with the electric resistance element so that the oxygen concentration in the atmosphere of the electric resistance element is controlled by said oxygen pump to thereby make it possible to detect the air/fuel ratio other than the stoichiometric composition.

9. A multi-functional sensor according to claim 8, wherein Me is Fe, and Mé is Ti.

10. An exhaust gas cleaning catalyst containing a composition consisting essentially of $Sr_{(1+x)/2}La_{(1-x)/2}Co_{1+x}Me_xO_{3-\delta}$ wherein $0 < x \leq 1$; δ represents loss of oxygen; and Me is at least one of Fe, Mn, Cr and V;

and $SrMéO_3$ wherein Mé is at least one of Ti, Zr and Hf.

11. An exhaust gas cleaning catalyst according to claim 10, wherein the amount of said $SrMéO_3$ is 60–70% by mole.

12. An exhaust gas cleaning catalyst according to claim 10, wherein x in the general formula is defined as $0 \leq x \leq 0.3$.

* * * * *